(12) United States Patent
Nakao et al.

(10) Patent No.: US 11,369,019 B2
(45) Date of Patent: Jun. 21, 2022

(54) ENDOSCOPE AND DISCHARGE CONTROL UNIT

(71) Applicant: OLYMPUS CORPORATION, Tokyo (JP)

(72) Inventors: Yosuke Nakao, Hino (JP); Kaoru Tsuruoka, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 390 days.

(21) Appl. No.: 16/713,148

(22) Filed: Dec. 13, 2019

(65) Prior Publication Data

US 2020/0120782 A1 Apr. 16, 2020

Related U.S. Application Data

(63) Continuation of application No. PCT/JP2018/015775, filed on Apr. 16, 2018.

(30) Foreign Application Priority Data

Jun. 30, 2017 (JP) .............................. JP2017-129045

(51) Int. Cl.
*H05F 3/04* (2006.01)
*A61B 1/00* (2006.01)
*G02B 23/24* (2006.01)

(52) U.S. Cl.
CPC ........... *H05F 3/04* (2013.01); *A61B 1/00124* (2013.01); *A61B 1/00128* (2013.01); *G02B 23/2476* (2013.01)

(58) Field of Classification Search
CPC ... A61B 1/07; A61B 1/00128; A61B 1/00114; A61B 1/0052; A61B 1/00071;
(Continued)

(56) References Cited

U.S. PATENT DOCUMENTS

2004/0092793 A1* 5/2004 Akai .................... A61B 1/05
600/134
2013/0050457 A1 2/2013 Murayama et al.
(Continued)

FOREIGN PATENT DOCUMENTS

CN 102958421 A 3/2013
EP 2 674 095 A1 12/2013
(Continued)

OTHER PUBLICATIONS

International Search Report dated Jul. 10, 2018 received in PCT/JP2018/015775.

*Primary Examiner* — Kevin J Comber
(74) *Attorney, Agent, or Firm* — Scully, Scott, Murphy & Presser, P.C.

(57) ABSTRACT

An endoscope includes: an internal conductor that is formed of a conductive material; an external conductor that is electrically insulated from the internal conductor and is formed of a conductive material that configures a part of an exterior; a holder that holds a first conductor that is electrically connected to the internal conductor and a second conductor that is electrically connected to the external conductor such that the first conductor and the second conductor are separated from each other by a space with a predetermined spatial distance; and a water-tightness holding member that holds water-tightness in the space.

17 Claims, 9 Drawing Sheets

(58) Field of Classification Search
CPC ..... A61B 1/00124; A61B 1/05; A61B 1/0055; H01T 4/10; H01T 4/04; G02B 23/2476; H05F 3/04
USPC ......................................................... 361/220
See application file for complete search history.

(56) References Cited

U.S. PATENT DOCUMENTS

2013/0303853 A1\* 11/2013 Takahashi ................ A61B 1/05
   600/134
2015/0303657 A1\* 10/2015 Jung .......................... H01T 4/04
   361/120

FOREIGN PATENT DOCUMENTS

| JP | H10-33463 A | 2/1998 |
| JP | 2004-148028 A | 5/2004 |
| JP | 5331949 B | 10/2013 |
| JP | 2014-054318 A | 3/2014 |
| WO | 2013/084548 A1 | 6/2013 |

\* cited by examiner

ENDOSCOPE AND DISCHARGE CONTROL UNIT

CROSS REFERENCE TO RELATED APPLICATION

This application is a continuation application of PCT/JP2018/015775 filed on Apr. 16, 2018 and claims benefit of Japanese Application No. 2017-129045 filed in Japan on Jun. 30, 2017, the entire contents of which are incorporated herein by this reference.

BACKGROUND OF THE INVENTION

1. Field of the Invention

The present invention relates to an endoscope provided with an external conductor that configures an exterior and a discharge control unit.

2. Description of the Related Art

An endoscope with a form in which an image pickup apparatus is provided at a distal end portion of an insertion portion that can be inserted into a living body, a machine, or the like as disclosed in Japanese Patent No. 5331949, for example, is known. There is also an endoscope in which a conductive member such as a metal frame is exposed to an exterior of an insertion portion as disclosed in Japanese Patent No. 5331949. The metal frame exposed to the exterior at the insertion portion of the endoscope is in a state in which the metal frame is not electrically connected to a ground potential in order to prevent an unintended current from flowing while an electric scalpel or the like is being used.

In a case in which a subject is charged with static electricity, for example, and the metal frame that is not electrically connected to the ground potential of the endoscope is brought into contact with the subject, the static electricity is applied to the metal frame. In this case, the static electricity is discharged from the metal frame to the image pickup apparatus, which is an electronic device disposed in the insertion portion and may become a reason of causing malfunction of the image pickup apparatus.

Japanese Patent No. 5331949 discloses a technology of providing, in the endoscope, a static electricity avoiding member for discharging the static electricity applied to the external conductor to an earth member that is electrically connected to the ground potential in order to prevent discharge to the image pickup apparatus. The static electricity avoiding member is a member that is electrically connected to the earth member and is disposed away from the metal frame by a predetermined spatial distance. In a case in which static electricity is applied to the metal frame, discharge occurs between the metal frame and the static electricity avoiding member.

SUMMARY OF THE INVENTION

An endoscope according to an aspect of the invention includes: an internal conductor that is formed of a conductive material; an external conductor that is electrically insulated from the internal conductor and is formed of a conductive material that configures a part of an exterior; a holder that holds a first conductor that is electrically connected to the internal conductor and a second conductor that is electrically connected to the external conductor such that the first conductor and the second conductor are separated from each other by a space with a predetermined spatial distance; and a water-tightness holding member that holds water-tightness in the space.

Also, a discharge control unit according to an aspect of the invention includes: an internal conductor that is formed of a conductive material; an external conductor that is electrically insulated from the internal conductor and is formed of a conductive material; a holder that holds a first conductor that is electrically connected to the internal conductor and a second conductor that is electrically connected to the external conductor such that the first conductor and the second conductor are separated from each other by a space with a predetermined spatial distance; and a water-tightness holding member that holds water-tightness in the space.

DETAILED DESCRIPTION OF THE PREFERRED EMBODIMENTS

Figure 1:
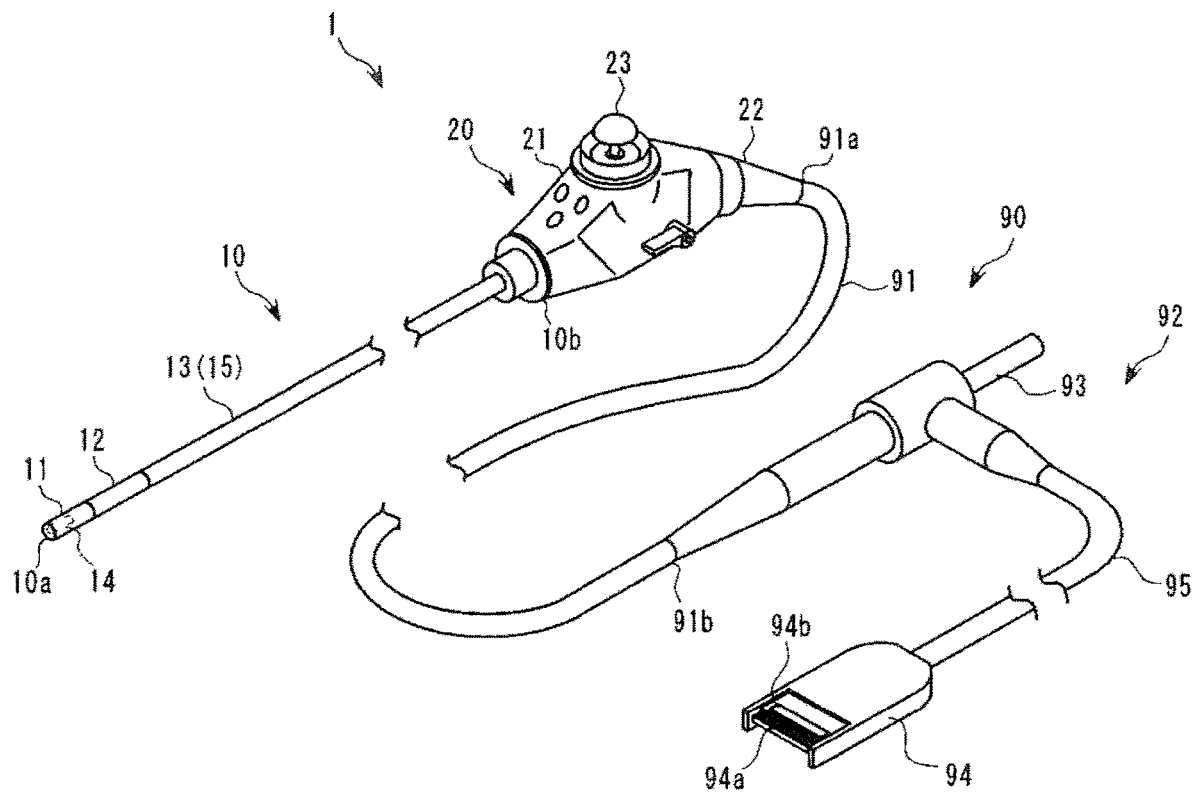
FIG. 1 is a diagram illustrating an outline of a configuration of an endoscope according to a first embodiment.

Hereinafter, preferred embodiments of the invention will be described with reference to drawings. Note that scales of the respective components are different in the respective drawings used in the following description in order to illustrate the respective components with recognizable sizes in the drawings, and that the invention is not limited to the numbers of components, the shapes of components, size ratios of components, and relative positional relationships of the respective components described in these drawings.

First Embodiment

FIG. 1 is a diagram illustrating an outline of a configuration of an endoscope 1 according to an embodiment. The endoscope 1 includes an insertion portion 10 that has an elongated shape to be inserted into a subject, an operation portion 20 that is continuous with a proximal end 10b of the insertion portion 10, and a universal cable 90 that extends from the operation portion 20. The endoscope 1 includes a discharge control unit 100, which will be described later. Note that the subject into which the insertion portion 10 is to be inserted may be a living thing such as a person or may be a non-living thing such as a machine or a building.

The insertion portion 10 is configured such that a distal end portion 11, a bending portion 12, and a tubular portion 13 are continuous with each other in an order from a distal end 10a toward the proximal end 10b.

An image pickup apparatus 14 to pick up images of an object such as inside of the subject is disposed at the distal end portion 11. The image pickup apparatus 14 includes a solid image pickup device, such as a CCD or a CMOS image sensor, and an objective lens. The distal end portion 11 is provided with an illumination window for emitting light for illuminating the object, which is not illustrated in the drawing. The illumination light emitted from the illumination window is emitted by a light source device, which is an external device of the endoscope 1, and reaches the illumination window through an optical fiber cable inserted into the insertion portion 10, which is not illustrated in the drawing. Since the image pickup apparatus 14 and the illumination window in the endoscope are known, detailed description of these components will be omitted.

The bending portion 12 is bent in accordance with motion of an operation stick 23 provided at the operation portion 20, which will be described later. Since a configuration of the bending portion 12 in the endoscope is known, detailed description of the bending portion 12 will be omitted.

The tubular portion 13 is a tubular section that couples a proximal end of the bending portion 12 to the operation portion 20, which will be described later. The tubular portion 13 may be in a rigid form that prevents the insertion portion 10 from being bent or may be in a flexible form that allows the insertion portion 10 to be bent along the subject into which the insertion portion 10 is inserted. An endoscope with an insertion portion in the rigid form is typically referred to as a rigid endoscope, and an endoscope with an insertion portion in the flexible form is typically referred to as a flexible endoscope. The rigid endoscope and the flexible endoscope are defined by ISO8600-1:2015 in the medical field, for example.

The insertion portion 10 includes, at least at a portion of an outer surface, an external conductor 15 made of a conductive material such as metal or a conductive resin. The external conductor 15 is electrically insulated from an internal conductor 16 (not illustrated in FIG. 1) that is disposed inside the endoscope 1 and is made of a conductive material such as metal or a conductive resin, as will be described later in detail. Here, the internal conductor 16 is a member that is electrically connected to a ground potential when the endoscope 1 is used.

In the embodiment, the tubular portion 13 is rigid, and the outer surface is configured of a tubular member made of metal in one example. Therefore, the outer surface of the tubular portion 13 configures the external conductor 15 in the embodiment. Note that external conductors 15 may also be disposed on outer surfaces of the distal end portion 11 and the bending portion 12.

In the embodiment, since the insertion portion 10 includes the external conductor 15, there is a probability that static electricity is applied from the subject to the external conductor 15 in a case in which the subject or the like charged with static electricity comes into contact with the external conductor 15.

Figure 2:
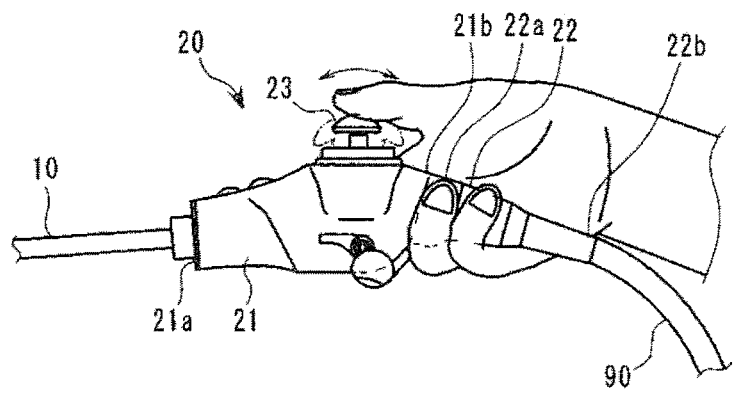
FIG. 2 is a diagram illustrating a state in which a grip of an operation portion is gripped with a right hand of a person.

The operation portion 20 includes a main body portion 21 to which the proximal end 10b of the insertion portion 10 is secured and a grip 22 that projects from the main body portion 21. FIG. 2 illustrates a state in which the grip 22 of the operation portion 20 is gripped with a right hand of a person.

The main body portion 21 has an outer surface made of an electrically insulated material such as a resin. The insertion portion 10 is secured to a distal end 21a of the main body portion 21, and the grip 22 is provided at a proximal end 21b of the main body portion 21 on the side opposite to the distal end 21a. The insertion portion 10 and the grip 22 extend in substantially opposite directions, respectively, from the main body portion 21.

The main body portion 21 is provided with the operation stick 23 that projects from the outer surface of the main body portion 21. The operation stick 23 is a member that can swing around a predetermined support point. A direction and an angle of bending of the bending portion 12 change in accordance with an inclination direction and an inclination angle of the operation stick 23 from a neutral position. The neutral position of the operation stick 23 is a predetermined position within a range in which the operation stick 23 can swing and indicates a position at which the shape of the bending portion 12 becomes a linear shape in the embodiment.

In the embodiment, the operation stick 23 is disposed in a surface along a longitudinal axis of the insertion portion 10 in the outer surface of the main body portion 21 in one example. A projecting direction of the operation stick 23 from the main body portion 21 in a case in which the operation stick 23 is at the neutral position substantially perpendicularly intersects the longitudinal direction of the insertion portion 10. Hereinafter, the surface of the main body portion 21 in which the operation stick 23 is provided will be referred to as an upper surface.

The grip 22 has a rod shape with a knife handle-like outer shape, and in the embodiment, the grip 22 can be gripped so as to be wrapped with a ring finger, a little finger, and a palm of a hand of a person as illustrated in FIG. 2 in one example. In the case in which the grip 22 is gripped, an index finger is located on the side of a distal end 22a of the grip 22 while the little finger is located on the side of a proximal end 22b of the grip 22. In the case in which the grip 22 is gripped, a thumb follows the upper surface of the main body portion 21, and a ball of the thumb can touch the operation stick 23.

The main body portion 21 and the grip 22 are hollow, and internal spaces of the main body portion 21 and the grip 22 communicate with an internal space of the insertion portion 10 with a tubular shape.

The universal cable 90 extends from the proximal end 22b of the grip 22. The universal cable 90 includes a flexible tube portion 91 and a connector portion 92.

The flexible tube portion 91 is an elongated tubular section with flexibility, and an electric cable, an optical fiber cable, or the like is inserted into the flexible tube portion 91. A distal end 91a of the flexible tube portion 91 is secured to the proximal end 22b of the grip 22 of the operation portion 20. The connector portion 92 is disposed at a proximal end 91b of the flexible tube portion 91.

The connector portion 92 is a section that connects the electric cable, the optical fiber cable, or the like to an external device of the endoscope 1. The connector portion 92 in the embodiment includes a light source connection portion 93 and an electrical connection portion 94.

The light source connection portion 93 can be attached to the light source device that emits illumination light. A proximal end of the optical fiber cable is exposed at the light source connection portion 93. The optical fiber cable is inserted into the operation portion 20 and the insertion portion 10 as described above. It is possible to deliver the illumination light emitted by the light source device to the illumination window provided at the distal end portion 11 of the insertion portion 10 through the optical fiber cable by attaching the light source connection portion 93 to the light source device.

The electrical connection portion 94 is a plug-shaped section provided with a plurality of electrical contact point portions and can be attached to a receptacle portion provided at a video processor, which is an external device of the endoscope 1. The plurality of electrical contact point portions included in the electrical connection portion 94 include a plurality of signal/power contact points 94*a* for exchanging signals and electric power between electronic devices included in the endoscope 1 and the video processor and one or more ground contact points 94*b* for connecting members included in the endoscope 1 to the ground potential.

The electronic devices included in the endoscope 1 include the image pickup apparatus 14, switches provided at the operation portion 20, and the like. The image pickup apparatus 14 and the video processor are electrically connected to each other via the electric cable inserted into the endoscope 1 by attaching the electrical connection portion 94 to the video processor.

The members that are included in the endoscope 1 and are electrically connected to the ground contact points 94*b* generally include a conductive shield member and the like for preventing radiation of electromagnetic waves from the electrical connection portion 94 and the like in addition to the aforementioned electronic devices such as an image pickup apparatus 14. The plurality of ground contact points 94*b* may be provided separately for being connected to the electronic devices and for being connected to shield members.

In the embodiment, the light source connection portion 93 and the electrical connection portion 94 are separated from each other, and a connection cable 95 with flexibility establishes connection between the light source connection portion 93 and the electrical connection portion 94. Note that in a case in which the light source device and the video processor are configured as the same device, for example, the light source connection portion 93 and the electrical connection portion 94 may be integrally configured.

An outer surface of the universal cable 90 is configured of an electrically insulated material such as a resin except for a part of the connector portion 92. Sections of the outer surface of the universal cable 90, which is configured of a conductive material such as metal, include a pipe sleeve for connecting the optical fiber cable to the light source device, the plurality of electrical contact point portions included in the electrical connection portion 94, and the like.

Figure 3:
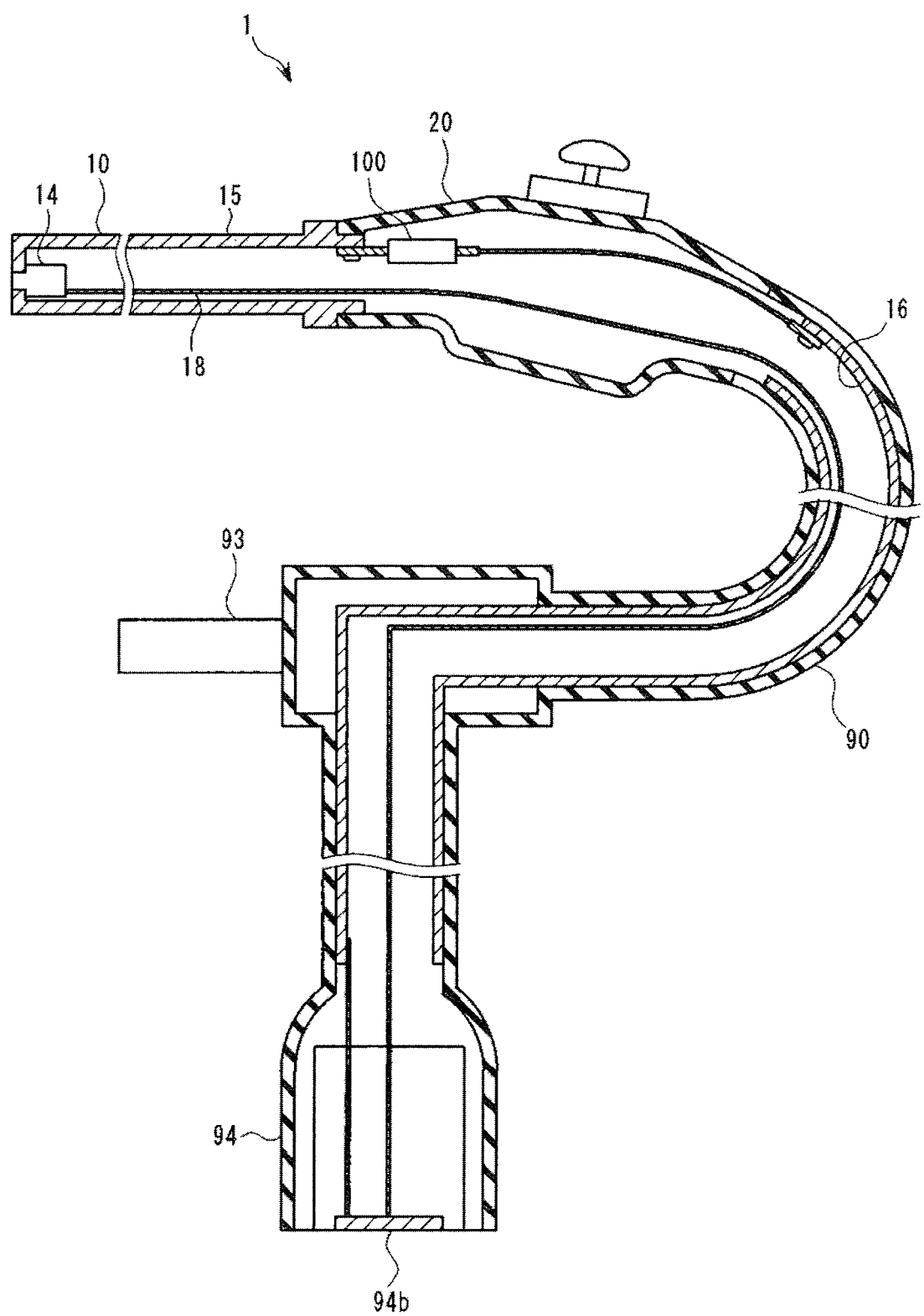
FIG. 3 is a diagram schematically illustrating members related to a ground contact point in the endoscope according to the first embodiment.

Next, a discharge control unit 100 included in the endoscope 1 will be described. FIG. 3 is a diagram schematically illustrating members related to the ground contact point 94*b* in the endoscope 1.

As described above, the image pickup apparatus 14 disposed at the insertion portion 10 is electrically connected to the signal/power contact points 94*a* and the ground contact points 94*b* of the electrical connection portion 94 via the electric cable inserted into the endoscope 1. FIG. 3 illustrates only an image pickup apparatus ground line 18 that electrically connects the image pickup apparatus 14 to the ground contact point 94*b*.

The internal conductor 16 that is electrically connected to the ground contact point 94*b* is disposed inside the endoscope 1. It is only necessary for the internal conductor 16 to be a member that is electrically connected to the ground contact point 94*b* and is made of a conductive material, and the shape and the position at which the internal conductor 16 is disposed are not particularly limited. The internal conductor 16 is a conductive shield member or the like that prevents radiation of electromagnetic waves from the frame made of metal disposed in the operation portion 20 and the universal cable 90, for example.

In the embodiment illustrated in FIG. 3, the internal conductor 16 is a sheath that is disposed in the universal cable 90 and is made of metal in one example. The sheath is obtained by shaping a net obtained by knitting a metal wire into a cylindrical shape and is disposed so as to surround the internal space of the universal cable 90.

As described above, the insertion portion 10 is provided with the external conductor 15 that configures a part of the exterior of the endoscope 1. The external conductor 15 is electrically insulated from the internal conductor 16.

Figure 4:
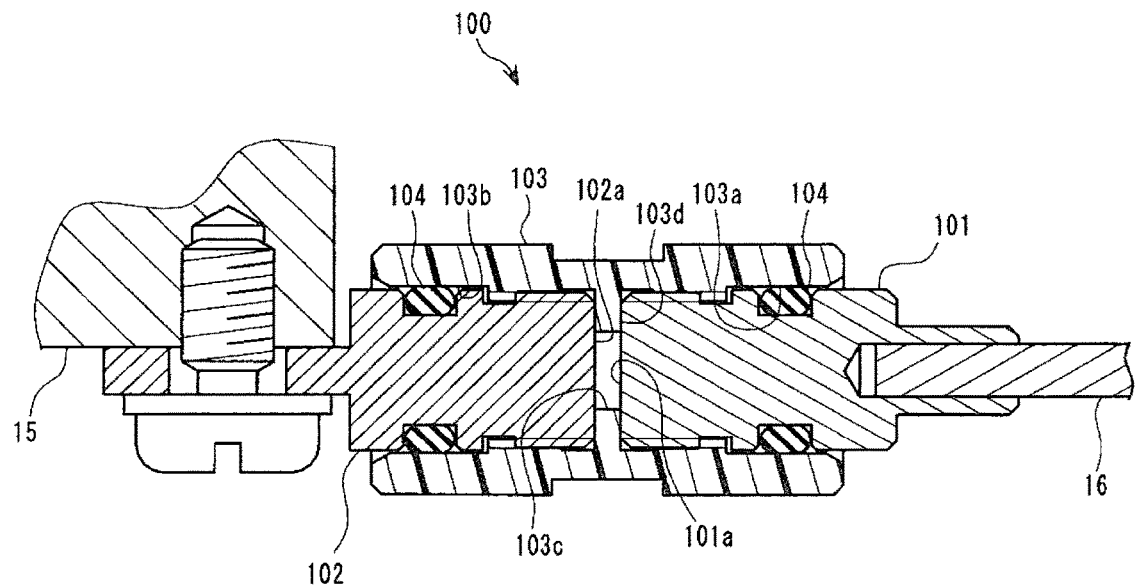
FIG. 4 is a sectional view of a discharge control unit according to the first embodiment.

The endoscope 1 in the embodiment includes the discharge control unit 100 that comes into contact with both the external conductor 15 and the internal conductor 16. FIG. 4 is a sectional view of the discharge control unit 100.

The discharge control unit 100 includes a first conductor 101, a second conductor 102, a holder 103, and a watertightness holding member 104.

The first conductor 101 is made of a conductive material such as metal and is electrically connected to the internal conductor 16. The second conductor 102 is made of a conductive material such as metal and is electrically connected to the external conductor 15.

The holder 103 is made of an electrically insulated material such as a resin and holds the first conductor 101 and the second conductor 102 in a state in which the first conductor 101 and the second conductor 102 are separated from each other by a predetermined spatial distance. The spatial distance is a shortest distance between the first conductor 101 and the second conductor 102 held in the separated state. Specifically, the holder 103 includes a first hole 103*a* into which the first conductor 101 is inserted, a second hole 103*b* into which the second conductor 102 is inserted, and a communication hole 103*c* that establishes communication between the first hole 103*a* and the second hole 103*b*. Note that it is desirable that the holder 103 have a configuration of positioning the first conductor 101 and the second conductor 102 in an abutting manner in order to minimize variations in distance by which the first conductor 101 and the second conductor 102 are separated from each other.

The first conductor 101 inserted into the first hole 103*a* and the second conductor 102 inserted into the second hole 103*b* face each other in a state in which the first conductor 101 and the second conductor 102 are separated from each other by the predetermined spatial distance through the communication hole 103*c*. In other words, the space in the communication hole 103*c* is a space that separates the first conductor 101 from the second conductor 102. Hereinafter, surfaces of the first conductor 101 and the second conductor 102 facing each other via the communication hole 103c will be referred to as facing surfaces 101a and 102a, respectively.

The water-tightness holding member 104 is a member that holds water-tightness in the communication hole 103c. The water-tightness holding member 104 prevents water or water vapor from entering the communication hole 103c from the outside of the discharge control unit 100 through a gap between the first hole 103a and the first conductor 101 and a gap between the second hole 103b and the second conductor 102.

The form of the water-tightness holding member 104 is not particularly limited. For example, the water-tightness holding member 104 may be a member with a cover shape or a container shape that covers an outer circumference of the discharge control unit 100. For example, the water-tightness holding member 104 may be a resin cured after the gap between the first hole 103a and the first conductor 101 and the gap between the second hole 103b and the second conductor 102 are filled with the resin.

Figure 5:
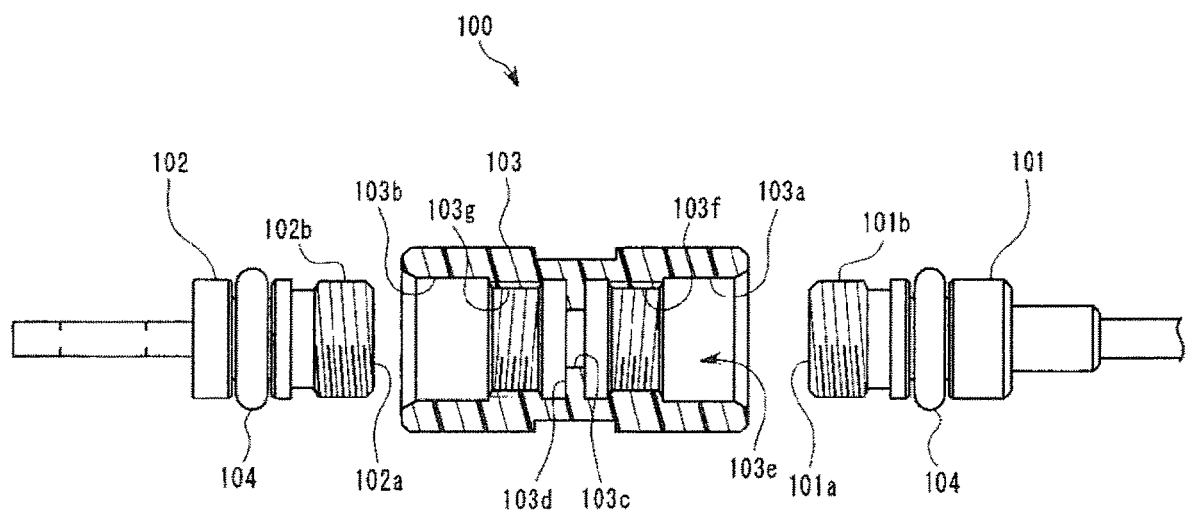
FIG. 5 is an exploded view of the discharge control unit according to the first embodiment.

A more specific configuration of the discharge control unit 100 according to the embodiment will be described. FIG. 5 is a diagram illustrating a state in which the discharge control unit 100 is exploded. In the embodiment, as illustrated in FIG. 5, the holder 103 is a cylindrical member that includes a linear and circular through-hole 103e, one opening of the through-hole 103e configures the first hole 103a, and the other opening of the through-hole 103e configures the second hole 103b. In other words, the first conductor 101 and the second conductor 102 are inserted into the holder 103 from both ends of the through-hole 103e formed in the cylindrical holder 103. The facing surface 101a of the first conductor 101 and the facing surface 102a of the second conductor 102 face each other in the through-hole 103e of the holder 103.

A spacer 103d that is inserted between the first conductor 101 and the second conductor 102 is disposed in the through-hole 103e of the holder 103. The spacer 103d is an annular member formed substantially coaxially with a central axis of the through-hole 103e. The spacer 103d is made of an electrically insulated material such as a resin. A space inside the annular spacer 103d configures the communication hole 103c. An inner diameter of the communication hole 103c formed in the spacer 103d is smaller than either an outer diameter of the facing surface 101a of the first conductor 101 or an outer diameter of the facing surface 102a of the second conductor 102.

Therefore, the facing surface 101a of the first conductor 101 and the facing surface 102a of the second conductor 102 abut on one end surface and the other end surface of the spacer 103d, respectively, in the through-hole 103e. Therefore, the spatial distance between the first conductor 101 and the second conductor 102 is defined by the thickness of the spacer 103d in the embodiment.

The spacer 103d may be a member separated from the holder 103 or may be a member integrated with the holder 103. In the embodiment, the spacer 103d is a member integrated with the holder 103 in one example. In other words, the spacer 103d is a plate-shaped section that projects inwardly in a radial direction and has a predetermined thickness in an axial direction in the through-hole 103e of the holder 103, and the communication hole 103c is formed at the spacer 103d.

Male screws 101b and 102b are formed in outer circumferential surfaces of the first conductor 101 and the second conductor 102, respectively. Female screws 103f and 103g to be screwed onto the male screws 101b and 102b are formed in the through-hole 103e of the holder 103 on both sides of the spacer 103d with the spacer 103d interposed between the female screws 103f and 103g.

Therefore, the first conductor 101 and the second conductor 102 are secured to the holder 103 in a state in which the first conductor 101 and the second conductor 102 are separated from each other by the predetermined spatial distance by screwing the first conductor 101 and the second conductor 102 into the through-hole 103e until the first conductor 101 and the second conductor 102 abut on the spacer 103d in the embodiment.

The water-tightness holding member 104 is an O-ring or a seal interposed between the respective outer circumferential surfaces of the first conductor 101 and the second conductor 102 and the through-hole 103e in the embodiment. The water-tightness holding member 104 is made of an elastically deformable material such as rubber and keeps water-tightness in the communication hole 103c by closely adhering to both the outer circumferential surfaces of the first conductor 101 and the second conductor 102 and the inner circumferential surface of the through-hole 103e. The material that configures the water-tightness holding member 104 has durability (steam resistance) against water vapor at a high temperature and at a high pressure in an autoclave sterilization treatment performed on the endoscope 1.

In the discharge control unit 100 according to the embodiment with the aforementioned configuration, the first conductor 101 that is electrically connected to the internal conductor 16 and the second conductor 102 that is electrically connected to the external conductor 15 face each other such that the first conductor 101 and the second conductor 102 are separated from each other by the predetermined spatial distance in the electrically insulated holder 103 with the container shape. Here, the first conductor 101 and the second conductor 102 are separated from each other by the space in the communication hole 103c.

Therefore, in a case in which a potential difference between the external conductor 15 and the internal conductor 16 is equal to or less than a predetermined value, electrical insulation between the external conductor 15 and the internal conductor 16 is secured. On the other hand, in a case in which static electricity is applied to the external conductor 15, the potential difference between the external conductor 15 and the internal conductor 16 exceeds the predetermined value, and discharge occurs between the first conductor 101 and the second conductor 102. In other words, since the static electricity applied to the external conductor 15 is delivered to the internal conductor 16 in the discharge control unit 100, the static electricity is prevented from being delivered to the image pickup apparatus 14 in the embodiment.

In the discharge control unit 100 according to the embodiment, the water-tightness in the space in the communication hole 103c with respect to the internal space in the endoscope 1 is held by the water-tightness holding member 104 being provided. Therefore, even in a case in which water vapor enters the internal space in the endoscope 1 when an autoclave sterilization treatment is performed on the endoscope 1, for example, the water vapor is prevented from entering a communication hole 103c. Therefore, in the discharge control unit 100 according to the embodiment, it is possible to prevent humidity in the communication hole 103c from changing and to constantly maintain the value of the potential difference between the first conductor 101 and the second conductor 102 depending on which discharge occurs between the first conductor 101 and the second conductor 102. In other words, in the discharge control unit 100 according to the embodiment, it is possible to prevent humidity in the communication hole 103c from changing and to always constantly maintain an upper limit value of the potential difference between the internal conductor 16 and the external conductor 15 with which electrical insulation between the internal conductor 16 and the external conductor 15 is maintained.

In the endoscope 1 according to the embodiment described above, it is possible to always constantly maintain the upper limit value of the potential difference between the internal conductor 16 and the external conductor 15 with which electrical insulation between the internal conductor 16 and the external conductor 15 is maintained regardless of a change in humidity in the internal space of the endoscope 1 and consequently to reliably maintain the state in which the external conductor 15 is electrically insulated from the ground potential during ordinary utilization. Also, in the endoscope 1 according to the embodiment, it is always possible to constantly maintain a lower limit value of the potential difference between the internal conductor 16 and the external conductor 15 depending on which short-circuiting (discharge) occurs between the internal conductor 16 and the external conductor 15 regardless of a change in humidity in the internal space of the endoscope 1 and consequently to reliably allow static electricity to escape to the internal conductor 16 and to prevent discharge of the static electricity to electronic devices such as an image pickup apparatus 14 from occurring in a case in which the static electricity is applied to the external conductor 15.

Figure 6:
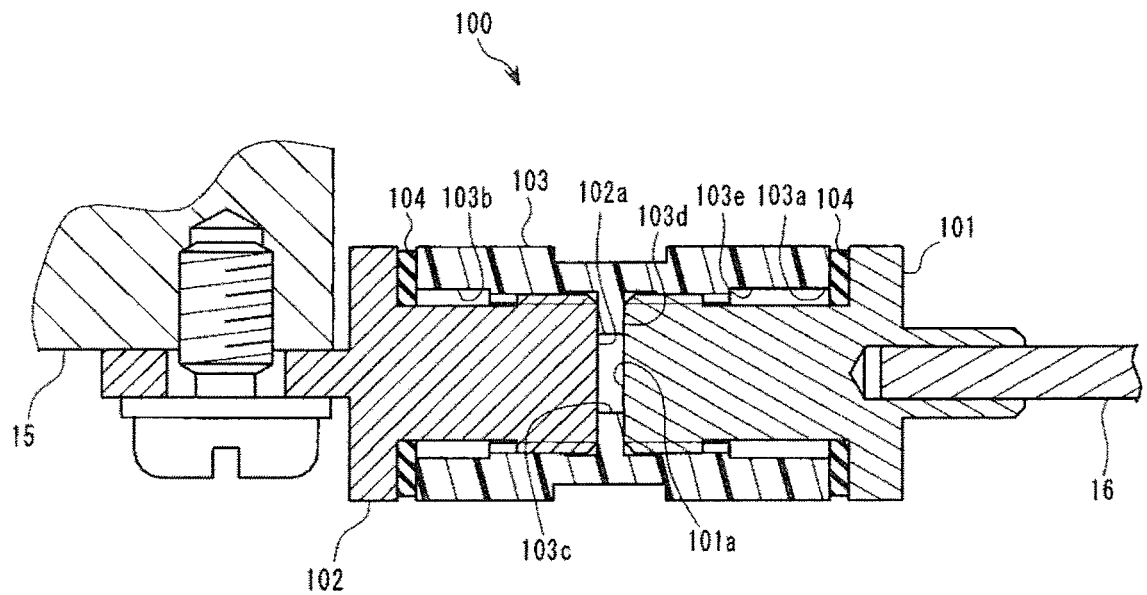
FIG. 6 is a sectional view illustrating a first modification of the discharge control unit according to the first embodiment.

FIG. 6 illustrates a first modification of the discharge control unit 100. In the first modification illustrated in FIG. 6, the water-tightness holding member 104 is a seal that is sandwiched between the holder 103 and the first conductor 101 and between the holder 103 and the second conductor 102, respectively.

Figure 7:
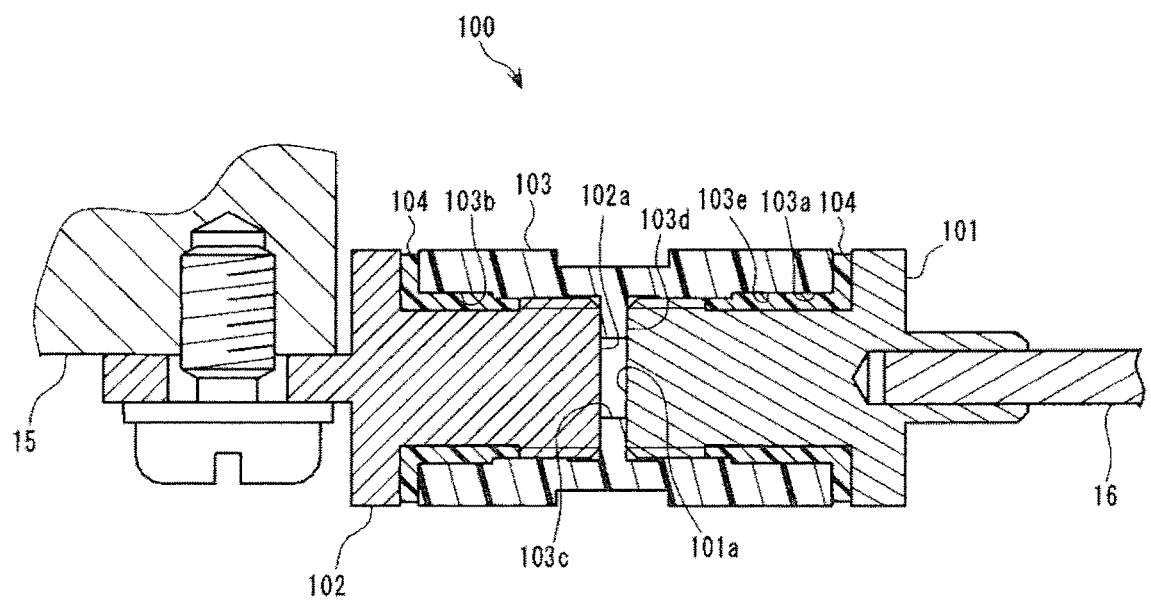
FIG. 7 is a sectional view illustrating a second modification of the discharge control unit according to the first embodiment.

FIG. 7 is a second modification of the discharge control unit 100. In the second modification illustrated in FIG. 7, the water-tightness holding member 104 is a resin cured after the gap between the holder 103 and the first conductor 101 and the gap between the holder 103 and the second conductor 102 are filled with the resin.

Water-tightness in the space in the communication hole 103c with respect to the internal space of the endoscope 1 can be held similarly to the aforementioned embodiment even in the discharge control units 100 according to both the modifications illustrated in FIGS. 6 and 7.

Second Embodiment

Hereinafter, a second embodiment of the invention will be described. Only differences from the first embodiment will be described below, the same reference numerals will be given to components that are similar to those in the first embodiment, and description of these components will appropriately be omitted.

Figure 8:
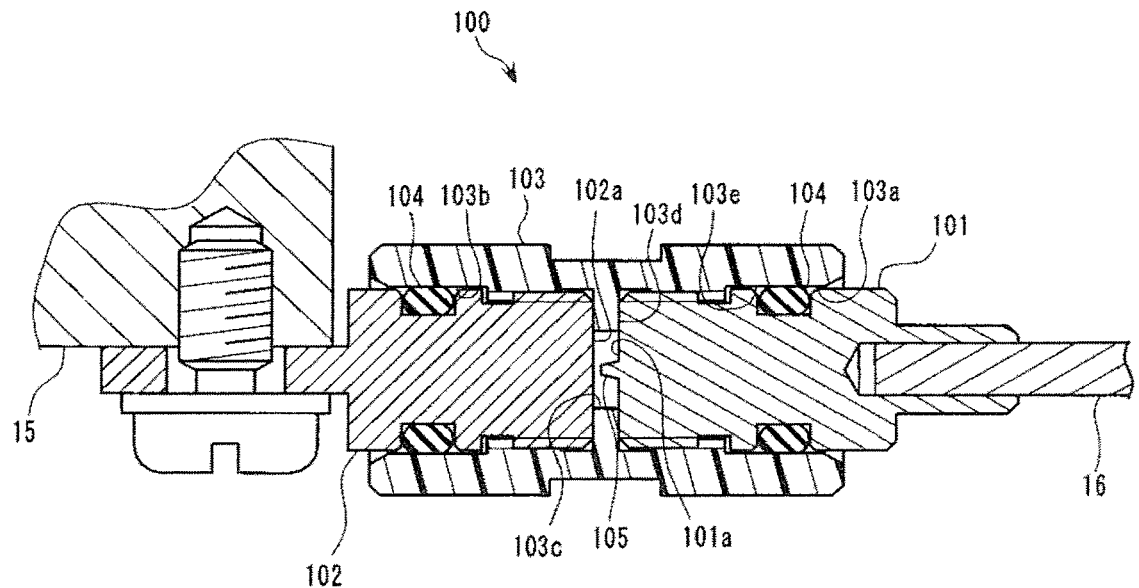
FIG. 8 is a sectional view of a discharge control unit according to a second embodiment.

FIG. 8 is a sectional view of a discharge control unit 100 according to the embodiment. As illustrated in FIG. 8, one or more projections 105 are formed at one of or both a facing surface 101a of a first conductor 101 and a facing surface 102a of a second conductor 102 in the discharge control unit 100 according to the embodiment. The projections 105 are made of a conductive material.

In the embodiment illustrated in the drawing, one projection 105 is provided in a standing manner at a center of the facing surface 101a of the first conductor 101 so as to project toward the facing surface 102a of the second conductor 102 in one example. It is possible to promote occurrence of discharge of static electricity between the first conductor 101 and the second conductor 102 by providing the projection 105 as in the embodiment.

It is possible to reliably prevent discharge of static electricity to electronic devices such as an image pickup apparatus 14 from occurring in the endoscope 1 according to the embodiment as well similarly to the first embodiment.

A water-tightness holding member 104 of the discharge control unit 100 according to the embodiment may be a seal as in the first modification of the first embodiment as illustrated in FIG. 6 or may be a resin with which the gaps are filled as in the second modification of the first embodiment as illustrated in FIG. 7.

Third Embodiment

Hereinafter, a third embodiment of the invention will be described. Only differences from the first embodiment will be described below, the same reference numerals will be given to components that are similar to those in the first embodiment, and description of these components will appropriately be omitted.

Figure 9:
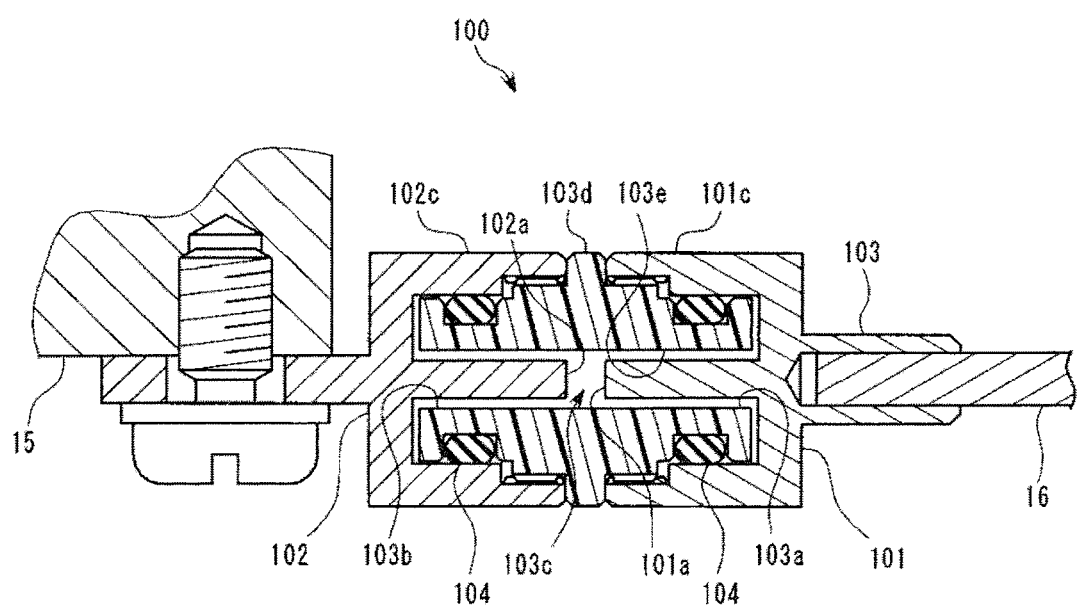
FIG. 9 is a sectional view of a discharge control unit according to a third embodiment.
Figure 10:
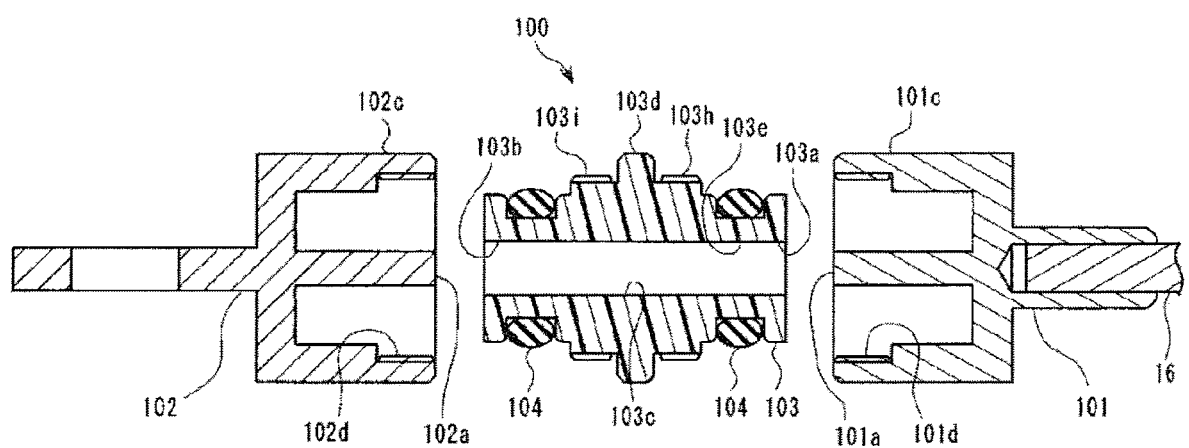
FIG. 10 is an exploded view of the discharge control unit according to the third embodiment.

FIG. 9 is a sectional view of a discharge control unit 100 according to the embodiment. FIG. 10 is an exploded view of the discharge control unit 100 according to the embodiment.

The discharge control unit 100 according to the embodiment is mainly different from that in the first embodiment in a position at which a spacer 103d is disposed. In the embodiment, the spacer 103d is disposed at an outer circumference of a holder 103.

The holder 103 in the embodiment is a cylindrical member that includes a linear and circular through-hole 103e. One opening of the through-hole 103e configures a first hole 103a into which a first conductor 101 is inserted, and the other opening of the through-hole 103e configures a second hole 103b into which a second conductor 102 is inserted. In the through-hole 103e of the holder 103, a facing surface 101a of the first conductor 101 and a facing surface 102a of the second conductor 102 face each other such that the facing surface 101a and the facing surface 102a are separated from each other by a predetermined spatial distance. In other words, a space between the facing surface 101a of the first conductor 101 and the facing surface 102a of the second conductor 102 in the through-hole 103e corresponds to a communication hole 103c.

The spacer 103d is an annular member disposed on an outer circumferential surface of the holder 103. The spacer 103d may be separated from the holder 103 or may be a flange-shaped member integrated with the holder 103. The spacer 103d has a predetermined thickness in an axial direction. In the embodiment, the spacer 103d is a flange-shaped member that projects outward in a radial direction from the outer circumferential surface of the holder 103 in one example.

Male screws 103h and 103i are formed on both sides of the spacer 103d in an axial direction with the spacer 103d interposed between the male screws 103h and 103i. A female screw 101d of the first conductor 101, which will be described later, is fitted onto the male screw 103h. A female screw 102d of the second conductor 102, which will be described later, is fitted onto the male screw 103i.

The first conductor 101 is provided with a cap portion 101c that covers the outer circumferential surface of the holder 103 and the first hole 103a. The cap portion 101c is a cylindrical-shape member that is opened on one side and is closed on the other side, and a section of the holder 103 at which the first hole 103a is opened can be inserted into the opening. In the state in which the holder 103 is inserted into the cap portion 101c, the facing surface 101a is located inside the through-hole 103e.

A distal end of the cap portion 101c is located on the same plane as the facing surface 101a. The cap portion 101c has such a depth that the holder 103 abuts on the spacer 103d in the case in which the holder 103 is inserted into the cap portion 101c. Also, the female screw 101d is formed in an inner circumferential surface of the cap portion 101c.

The second conductor 102 is provided with a cap portion 102c that covers the outer circumferential surface of the holder 103 and the second hole 103b. The cap portion 102c is a cylindrical-shaped member that is opened on one side and is closed on the other side, and a section of the holder 103 at which the second hole 103b is opened can be inserted into the opening. In the state in which the holder 103 is inserted into the cap portion 102c, the facing surface 102a is located inside the through-hole 103e.

A distal end of the cap portion 102c is located on the same plane as the facing surface 102a. The cap portion 102c has such a depth that the holder 103 abuts on the spacer 103d in the case in which the holder 103 is inserted into the cap portion 102c. Also, the female screw 102d is formed in an inner circumferential surface of the cap portion 102c.

In the embodiment, the facing surface 101a of the first conductor 101 and the facing surface 102a of the second conductor 102 are secured to the holder 103 in a state in which the facing surface 101a and the facing surface 102a are separated from each other by the predetermined spatial distance by screwing the first conductor 101 and the second conductor 102 into the holder 103 until the distal end of the cap portion 101c of the first conductor 101 and the distal end of the cap portion 102c of the second conductor 102 abut on the spacer 103d.

In this manner, the distal end of the cap portion 101c of the first conductor 101, the distal end of the cap portion 102c of the second conductor 102, and the spacer 103d are members that define the spatial distance between the first conductor 101 and the second conductor 102 in the embodiment.

It is easy to perform working with high precision such that the distal end of the cap portion 101c of the first conductor 101 and the facing surface 101a are located on the same plane. Similarly, it is also easy to perform working with high precision such that the distal end of the cap portion 102c of the second conductor 102 and the facing surface 102a are located on the same plane. Therefore, it is possible to curb variations in positioning of the facing surface 101a of the first conductor 101 and the facing surface 102a of the second conductor 102, which are hidden inside the holder 103 in a state in which the discharge control unit 100 is assembled, according to the embodiment.

The water-tightness holding member 104 is an O-ring or a seal that is interposed between the respective inner circumferential surfaces of the cap portion 101c of the first conductor 101 and the cap portion 102c of the second conductor 102 and the outer circumferential surface of the holder 103 in the embodiment.

In the discharge control unit 100 according to the embodiment as described above, water tightness in the space in the communication hole 103c with respect to the internal space of the endoscope 1 is held similarly to the first embodiment. Therefore, in the endoscope 1 according to the embodiment, it is possible to always constantly maintain an upper limit value of a potential difference between the internal conductor 16 and the external conductor 15 with which electrical insulation between the internal conductor 16 and the external conductor 15 is maintained regardless of a change in humidity in the internal space of the endoscope 1 and consequently to reliably maintain a state in which the external conductor 15 is electrically insulated from the ground potential during ordinary utilization. Also, in the endoscope 1 according to the embodiment, it is possible to always constantly maintain a lower limit value of the potential difference between the internal conductor 16 and the external conductor 15 depending on which short-circuiting (discharge) occurs between the internal conductor 16 and the external conductor 15 regardless of a change in humidity in the internal space of the endoscope 1 and consequently to reliably allow static electricity to escape to the internal conductor 16 and to prevent discharge of the static electricity to electronic devices such as an image pickup apparatus 10 from occurring in a case in which the static electricity is applied to the external conductor 15.

In the discharge control unit 100 according to the embodiment, outer circumferential surfaces of the cap portion 101c of the first conductor 101, the spacer 103d, and the cap portion 102c of the second conductor 102 are more preferably covered with an electrically insulated material such as a resin. A configuration of the covering member that covers the outer circumferential surfaces of the cap portion 101c of the first conductor 101, the spacer 103d, and the cap portion 102c of the second conductor 102 and is made of an electrically insulated material is not particularly limited. For example, the covering member may be formed by winding a tape-shaped film around the outer circumferential surfaces or may be formed by covering the outer circumferential surfaces with a tube. Alternatively, the covering member may be formed by curing a resin such as an adhesive material applied to the outer circumferential surfaces, for example. It is more preferable to provide the covering member since it is possible to further improve the water-tightness in the space in the communication hole 103c.

In the discharge control unit 100 according to the embodiment, one or more projections may be formed at one of or both the facing surface 101a of the first conductor 101 and the facing surface 102a of the second conductor 102 similarly to the second embodiment. By providing the projections, it is possible to promote occurrence of discharge of static electricity between the first conductor 101 and the second conductor 102.

Fourth Embodiment

Hereinafter, a fourth embodiment of the invention will be escribed. Only differences from the first embodiment will be described below, the same reference numerals will be given to components that are similar to those in the first embodiment, and description of these components will appropriately be omitted.

Figure 11:
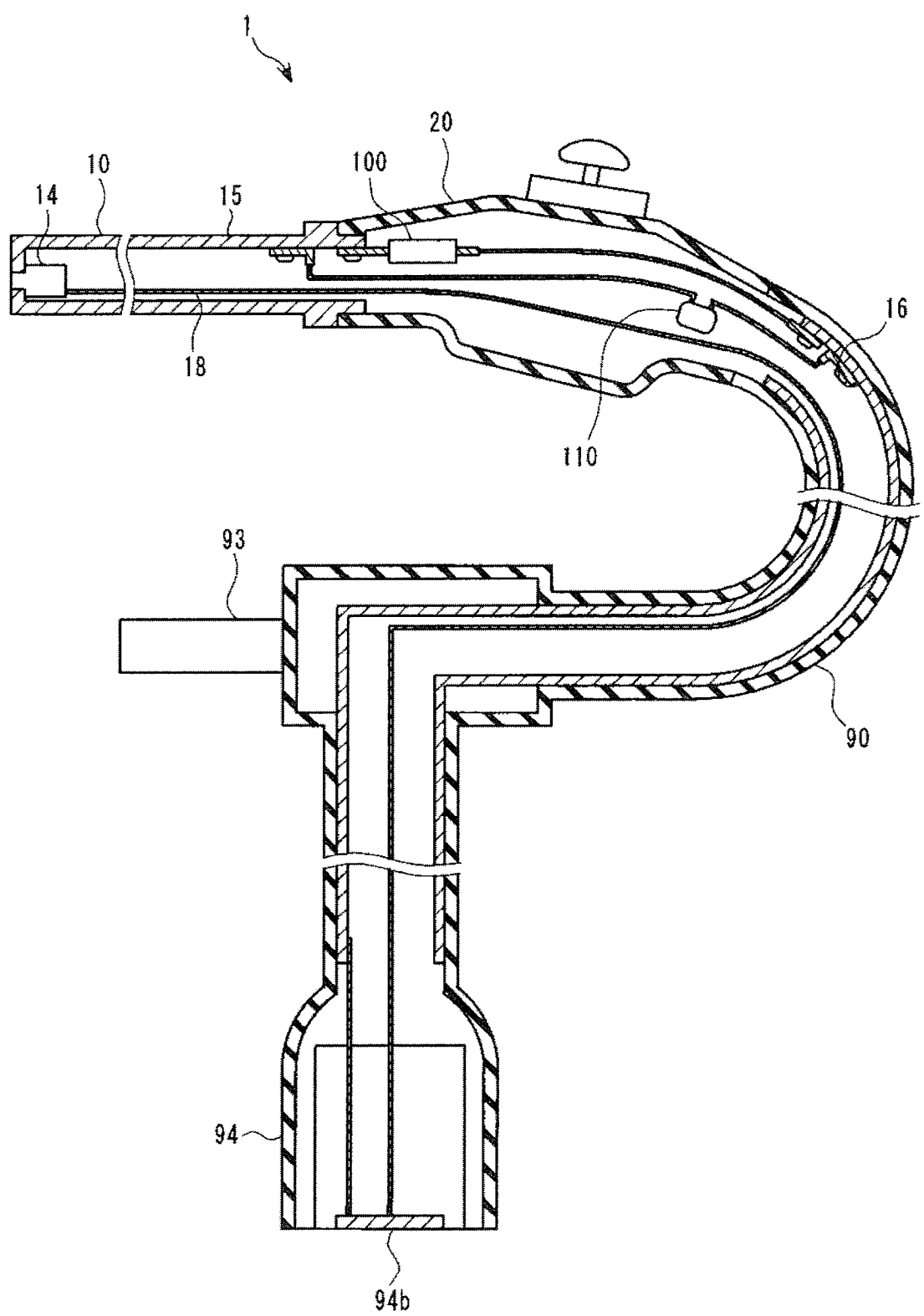
FIG. 11 is a diagram schematically illustrating members related to a ground contact point in an endoscope according to a fourth embodiment.

FIG. 11 is a diagram schematically illustrating members related to a ground contact point 94b. As illustrated in FIG. 11, an endoscope 1 according to the embodiment includes, inside, a capacitor 110 that is electrically connected to an external conductor 15 and an internal conductor 16.

Results of experiment conducted by the applicants have proved that discharge of static electricity in a discharge control unit 100 is likely to occur if the capacitor 110 is provided between the external conductor 15 and the internal conductor 16 as in the embodiment. Therefore, it is possible to reliably prevent discharge of static electricity to electronic devices such as an image pickup apparatus 14 from occurring in the endoscope 1 according to the embodiment.

In the discharge control unit 100 according to the embodiment, one or more projections 105 may be formed at one of or both a facing surface 101a of the first conductor 101 and a facing surface 102a of the second conductor 102 as described above in the second embodiment.

Fifth Embodiment

Hereinafter, a fifth embodiment of the invention will be described. Only differences from the first embodiment will be described below, the same reference numerals will be given to components that are similar to those in the first embodiment, and description of these components will appropriately be omitted.

Figure 12:
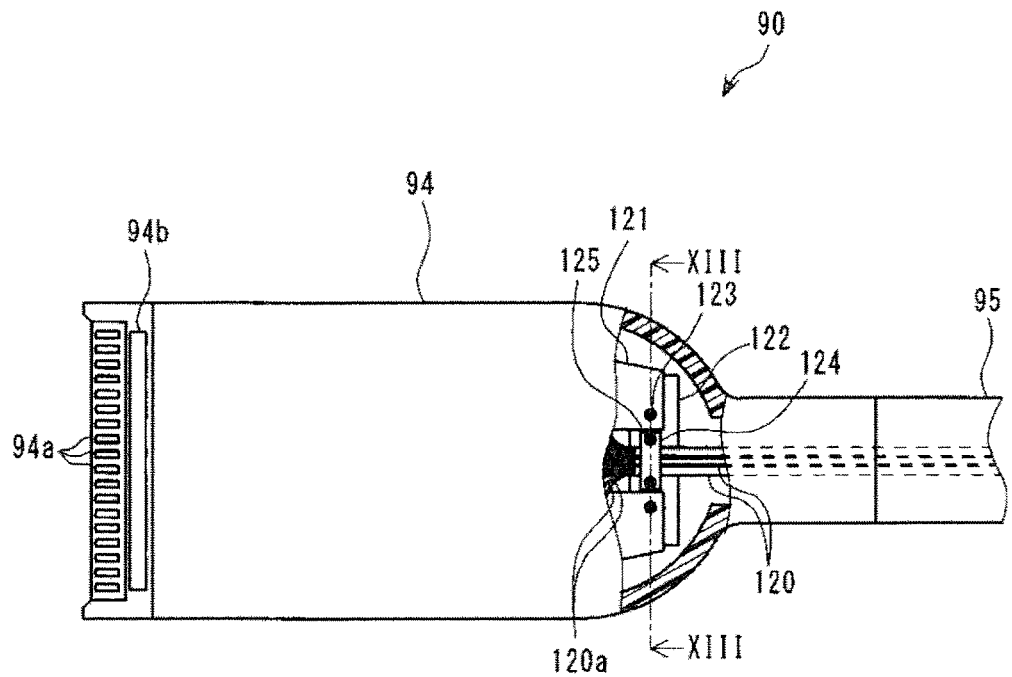
FIG. 12 is a partial sectional view of an electrical connection portion in the endoscope according to the fourth embodiment.
Figure 13:
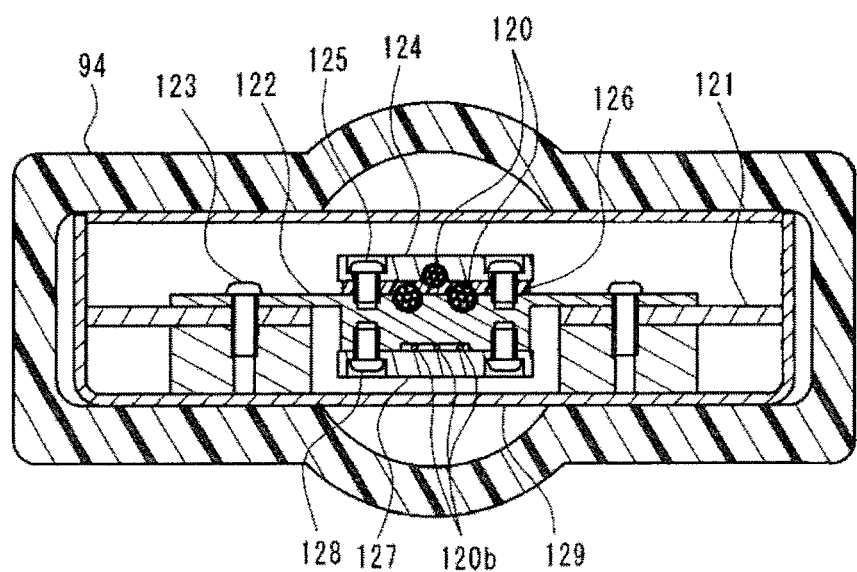
FIG. 13 is a sectional view along XIII-XIII in FIG. 12.

FIG. 12 is a partial sectional view of an electrical connection portion 94 in an endoscope 1 according to the embodiment. FIG. 13 is a sectional view along XIII-XIII in FIG. 12.

As illustrated in FIG. 12, each of a plurality of electric cables 120 inserted into a universal cable 90 includes a plurality of core lines 120a for delivering signals and power. Ends of the core lines 120a of each electric cable is soldered to a land of a relay board 121 disposed in an electrical connection portion 94. The core lines 120a of each electric cable 120 are electrically connected to signal/power contact points 94a via a circuit formed on the relay board 121. The relay board 121 is secured to the inside of the electrical connection portion 94 with a plurality of screws, which are not illustrated in the drawing.

If the arrangement shape of the core lines 120a changes in the electrical connection portion 94, there is a probability that the core lines 120a are short-circuited. Therefore, positions of the electric cables 120 relative to the relay board 121 are fixed in the electrical connection portion 94.

Hereinafter, a configuration of securing the electric cables 120 to the relay board 121 will be described. As illustrated in FIG. 13, a platform 122 is secured to the relay board 121 with a plurality of screws 123.

The electric cables 120 are secured to the platform 122 by being sandwiched between the platform 122 and a pressing plate 124 secured to the platform 122 with a plurality of screws 125. In other words, the electric cables 120 are secured to the relay board 121 with this configuration.

Here, in the embodiment, a silicone sheet 126 is interposed between the platform 122 and the pressing plate 124. The electric cables 120 are secured to the same positions as those at the time of the beginning of fastening due to elasticity of the silicone sheet 126 even if the pressing plate 124 slightly deviates when the screws 125 are fastened. Also, the elasticity of the silicone sheet 126 can prevent abrasion of an outermost surfaces of the electric cables 120 caused by the electric cables 120 sandwiched with hard articles. Therefore, it is possible to prevent the arrangement shapes of the core lines 120a from being deformed due to fastening of the screws 125 in the embodiment.

In the embodiment, the platform 122 is configured of a conductive material such as metal, and the platform 122 comes into contact with a land that is electrically connected to a ground contact points 94b of the relay board 121.

A shield line pressing plate 127 is secured to the platform 122 with a plurality of screws 128. Shield lines 120b of the electric cables 120 are sandwiched between the platform 122 and the shield line pressing plate 127. The platform 122 comes into contact with a shield member 129 that is disposed so as to surround the relay board 121, the core lines 120a, and the like and is made of a conductive material such as metal.

Figure 14:
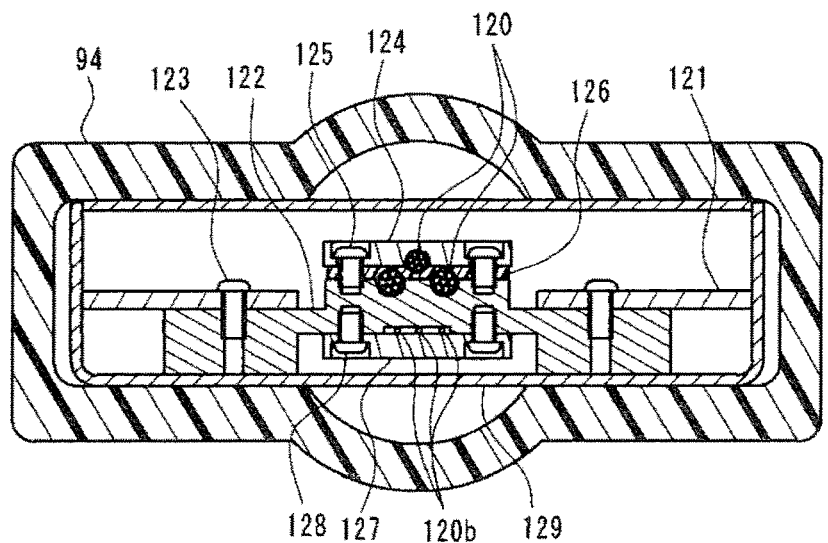
FIG. 14 is a diagram illustrating a modification of an electrical connection portion according to a fifth embodiment.

In this manner, the platform 122 also serves as a member that electrically connect the member for shielding electromagnetic waves at the electrical connection portion 94 and the electric cables 120 to the ground contact points 94b. Note that although the platform 122 is configured to sandwich the relay board 121 between a plurality of members screwed with the screws 123 in the embodiment, the platform 122 may be a single component and may be configured to sandwich the relay board 121 with head portions of the screws 123 as illustrated as a modification in FIG. 14. According to the modification illustrated in FIG. 14, it is possible to reduce the number of components that configure the electrical connection portion 94.

Sixth Embodiment

Hereinafter, a sixth embodiment of the invention will be described. Only differences from the first embodiment will be described below, the same reference numerals will be given to components that are similar to those in the first embodiment, and description of these components will appropriately be omitted.

Figure 15:
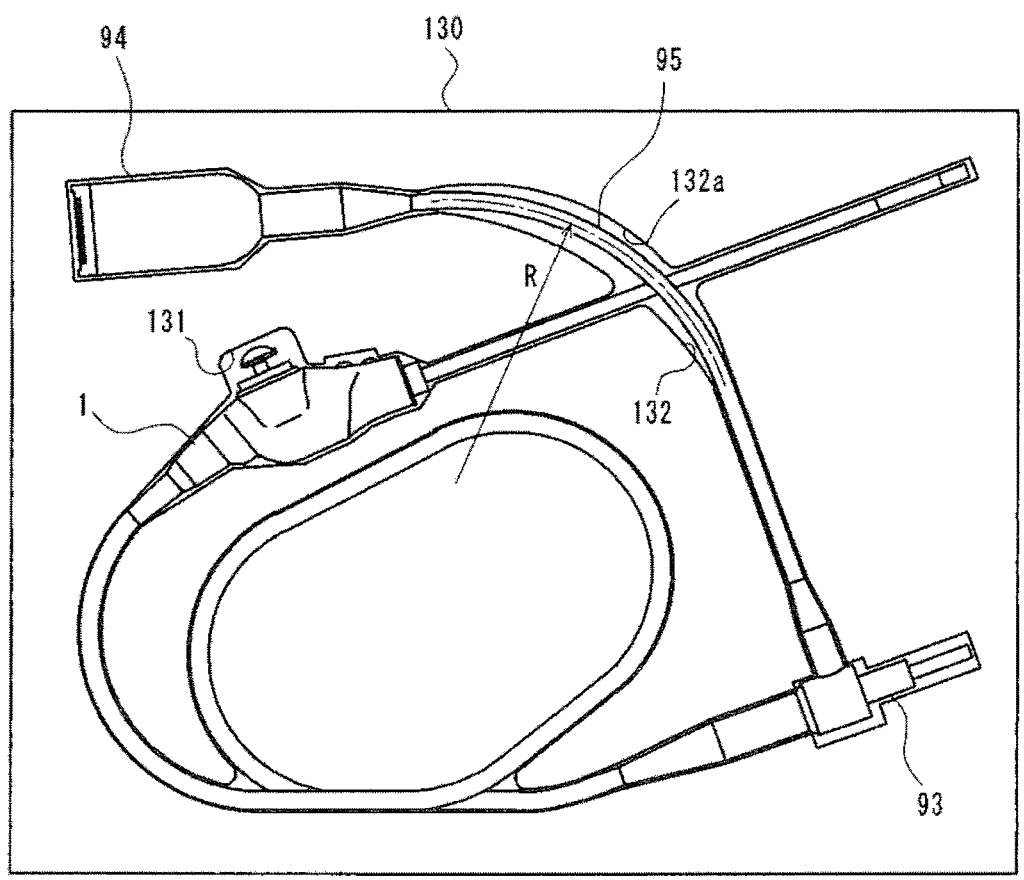
FIG. 15 is a diagram illustrating a packaging member that accommodates an endoscope according to a sixth embodiment.

FIG. 15 is a diagram illustrating a packaging member 130 in a case that accommodates an endoscope 1 according to the embodiment. As illustrated in FIG. 15, the packaging member 130 includes a recessed portion 131 into which the endoscope 1 is fitted. The recessed portion 131 has a shape that substantially follows an outer shape of the endoscope 1 and restricts movement of the endoscope 1 inside the recessed portion 131.

The packaging member 130 according to the embodiment includes a connection cable accommodation groove 132 that includes a bending portion 132a in which a part of a connection cable 95 connecting a light source connection portion 93 of a universal cable 90 to an electrical connection portion 94 is accommodated at a predetermined radius of curvature.

A central axis C of the bending portion 132a of the connection cable accommodation groove 132 has a shape bent at a predetermined radius of curvature R, and the width of the bending portion 132a is widened both inward and outward in the radial direction such that the width of the bending portion 132a is wider than the width of the connection cable 95.

By the bending portion 132a being widened both inward and outward in the radial direction, it is possible to accommodate the universal cable 90 in the recessed portion 131 without applying a tensile force (force of both pulling and compressing) to the connection cable 95 even in a case in which the length of the connection cable 95 varies. If a tensile force is applied to the connection cable 95, a force, such as pulling, compression, or twisting is applied to the electric cable inserted into the connection cable 95, and there is thus a probability that this may cause malfunctions such as disconnection of the electric cable and a contact failure at a connecting portion between the electric cable and the board. Preferably, the packaging member according to the embodiment can prevent a tensile force from being generated at the connection cable 95.

In the embodiment, it is possible to prevent a tensile force from being generated at the connection cable 95 even in a case in which at least one of the light source connection portion 93 and the electrical connection portion 94 moves in the recessed portion 131 since the bending portion 132a is widened both inward and outward in the radial direction.

Also, the invention is not limited to the aforementioned embodiments, appropriate changes can be made without departing from the gist or idea of the invention that can be read in the claims and the entire specification, and endoscopes achieved by adding such changes are also included in the technical scope of the invention.

What is claimed is:

1. An endoscope comprising:
an internal conductor formed of a conductive material;
an external conductor electrically insulated from the internal conductor, the external conductor being formed of a conductive material that configures a part of an exterior;
a holder that holds a first conductor electrically connected to the internal conductor and a second conductor electrically connected to the external conductor such that the first conductor and the second conductor are separated from each other by a space with a predetermined distance interposed between the first conductor and the second conductor; and
a seal configured to hold water tightness in the space;
wherein the holder comprises:
a first hole into which the first conductor is inserted,
a second hole into which the second conductor is inserted, and
a communication hole communicating with both of the first hole and the second hole, the first conductor and the second conductor facing each other and being separated from each other by the predetermined distance through the communication hole, and
the seal holds water-tightness in the communication hole with respect to an outside of the holder.

2. The endoscope according to claim 1, wherein one or more of the first conductor and the second conductor having one or more projections projecting into the communication hole.

3. The endoscope according to claim 1, further comprising a capacitor electrically connected to the internal conductor and to the external conductor.

4. The endoscope according to claim 1, wherein the seal comprises a first seal located between the holder and the second conductor and a second seal located between the holder and the first conductor.

5. The endoscope according to claim 1, wherein the seal covers at least the holder.

6. The endoscope according to claim 1, further comprising:
an insertion portion,
wherein the exterior is an outer surface of the insertion portion.

7. The endoscope according to claim 1,
wherein the first conductor and the first hole are screwed to each other through respective screws formed at the first conductor and the first hole, and
the second conductor and the second hole are screwed to each other through respective screws formed at the second conductor and the second hole.

8. The endoscope according to claim 1, wherein the predetermined distance is configured such that when a potential difference between the internal conductor and the external conductor exceeds a predetermined value, a discharge occurs between the first conductor and the second conductor via the space.

9. The endoscope according to claim 1, wherein the space is an air gap.

10. The endoscope according to claim 1, wherein the communication hole having a smaller inner diameter than an inner diameter or each of the first and second holes to define first and second stops defining the predetermined distance when the first and second conductors abut the first and second stops, respectively.

11. A discharge control unit comprising:
an internal conductor formed of a conductive material;
an external conductor electrically insulated from the internal conductor the external conductor being formed of a conductive material;
a holder that holds a first conductor electrically connected to the internal conductor and a second conductor electrically connected to the external conductor such that the first conductor and the second conductor are separated from each other by a space with a predetermined distance interposed between the first conductor and the second conductor; and
a seal configured to hold water-tightness in the space;
wherein the holder comprises:
a first hole into which the first conductor is inserted,
a second hole into which the second conductor is inserted, and
a communication hole communicating with both of the first hole and the second hole, the first conductor and the second conductor facing each other and being separated from each other by the predetermined distance through the communication hole, and
the seal holds water-tightness in the communication hole with respect to an outside of the holder.

12. The discharge control unit according to claim 11, wherein one or more of the first conductor and the second conductor having one or more projections projecting into the communication hole.

13. The discharge control unit according to claim 11,
wherein the first conductor and the first hole are screwed to each other through respective screws formed at the first conductor and the first hole, and
the second conductor and the second hole are screwed to each other through respective screws formed at the second conductor and the second hole.

14. The discharge control unit according to claim 11, further comprising a capacitor electrically connected to the internal conductor and to the external conductor.

15. The discharge control unit according to claim 11, wherein the predetermined distance is configured such that when a potential difference between the internal conductor and the external conductor exceeds a predetermined value, a discharge occurs between the first conductor and the second conductor via the space.

16. The discharge control unit according to claim 11, wherein the space is an air gap.

17. The discharge control unit according to claim 11, wherein the communication hole having a smaller inner diameter than an inner diameter or each of the first and second holes to define first and second stops defining the predetermined distance when the first and second conductors abut the first and second stops, respectively.

* * * * *